United States Patent [19]
Kluger et al.

[11] Patent Number: 6,067,986
[45] Date of Patent: May 30, 2000

[54] METHOD AND APPARATUS EMPLOYING MOTOR MEASURES FOR EARLY DIAGNOSIS AND STAGING OF DEMENTIA

[76] Inventors: Alan Kluger, 11871 84th Ave. Apt. 404, Kew Gardens, N.Y. 11415; John Gianutsos, 38-25 52nd St., Sunnyside, N.Y. 11104; Barry Reisberg, 20 Waterside Plz., #7K, New York, N.Y. 10010

[21] Appl. No.: 08/145,984

[22] Filed: Oct. 29, 1993

[51] Int. Cl.$^7$ .................................................. A61B 5/03
[52] U.S. Cl. ............................................................ 128/782
[58] Field of Search ................................... 128/745, 774, 128/782

[56] References Cited

U.S. PATENT DOCUMENTS

| | | | |
|---|---|---|---|
| 4,416,293 | 11/1983 | Anderson et al. | 128/782 |
| 4,586,515 | 5/1986 | Berger | 128/782 |
| 5,080,109 | 1/1992 | Arme et al. | 128/782 |
| 5,203,346 | 4/1993 | Fahr et al. | 128/782 |
| 5,305,764 | 4/1994 | Yamada et al. | 128/745 |
| 5,365,941 | 11/1994 | Yoshimatsu et al. | 128/745 |

OTHER PUBLICATIONS

Instructions and Normative Data for Model 32020 Purdue Pegboard, Dr. Alan Kluger, Lafayette Instrument Co. pp. 1–24 1986.

Longitudinal Changes: Progressive Idiopathic Dementia, chp. 29, Robert S. Wilson, Alfred W. Kaszniak, pp. 285–293 1986.

MRI–Detected White Matter Lesions are Associated With Impairment in Higher Order Motor Control in Normal Human Aging, A. Kluger, J. Gianutsos, et al., Society for Neuroscience Abstracts, 19, 1993, 180.

Abstract Forms: Expanded Summary: Motor Impairment in Mild Cognitive Decline and Early Alzheimer's Disease (Kluger, Gianutsos, de Leon et al.), Abstracts for the 46th Meeting of "The Gerontological Society of America", Nov. 19–23, 1993, New Orleans, LA.

The Global Deterioration Scale for Assessment of Primary Degenerative Dementia, Barry Reisberg, Steve H. Ferris, et al., Am J Psychiatry 139;9, Sep. 1982, pp. 1136–1139.

Computerized Cognitive Assessment Systems; NYU Computerized Test Battery for Assessing Cognition in Aging and Dementia, Steven H. Ferris, Charles Flicker, Barry Reisberg, vol. 24, No. 4, 1988, pp. 699–702.

Letters to the Editor; Proposed Method for Analyzing Carotid Endarterectomy Results; Eugene F. Bernstein, Saran Jonas, Alan Kluger, Rajesh M. Parikh, Stroke vol. 19, No. 3, Aug., 1988, pp. 1054–1055.

Patterns of Declining Memory, Jeanne G. Gilbert, Raymond F. Levee, Journal of Gerontology, 1971, vol. 26, No. 1, pp. 70–75.

Regular Articles; A New Rating Scale for Alzheimer's Disease, Wilma G. Rosen, Richard C. Mohs, Kenneth L. Davis; Am J Psychiatry 141:11, Nov., 1984, pp. 1356–1364.

"Mini–Mental State"—A Practical Method for Grading the Cognitive State of Patients for the Clinician, Marshal F. Folstein, Susan E. Folstein, Paul R. McHugh; J. Psychiat. Res. 1975, vol. 12, pp. 189–198.

The Association Between Quantitative Measures of Dementia and of Senile Change in the Cerebral Grey Matter of Elderly Subjects, G. Blessed, B.E. Tomlinson, Martin Roth, Am J Psychiatry, (1968), 114, pp. 797–811.

(List continued on next page.)

*Primary Examiner*—Max Hindenburg
*Attorney, Agent, or Firm*—Gottlieb, Rackman & Reisman, P.C.

[57] ABSTRACT

A method for differentiating cognitively normal elderly individuals from mildly demented patients with Alzheimer's disease by monitoring motor/psychomotor test results by the use of various computer monitored transducer apparatus attached to the individual while the individual undergoes testing. Head tracking ability, head steadiness, EMG-Arm extension tracking, and joint position matching are measured parameters used in the method.

4 Claims, 3 Drawing Sheets

OTHER PUBLICATIONS

Drug Development Research 15:101–114; Stage–Specific Behavioral, Cognitive, and In Vivo Changes in Community Residing Subjects with Age–Associated Memory Impairment and Primary Degenerative Dementia of the Alzheimer Type, Barry Reisberg, Steven H. Ferris, Mony J. deLeon et al., 1988 Alan R. Liss, Inc., pp. 101–114.

Early Marker for Alzheimer's Disease: The Atrophic Hippocampus, Mony J. de Leon, Ajax E. George, et al., The Lancet, Sep. 16, 1989, pp. 672–673.

Abstract: White Matter Lesions in Human Aging: Associations with Higher Order Motor Control, A. Kluger, J. Gianutsos, J. Golomb, et al., Amerian Neuropsychiatric Association Sixth Annual Meeting, Jul., 1994, NYU Medical Center.

Cognition–Independent Neurologic Symptoms in Normal Aging and Probable Alzheimer's Disease, Emile H. Franssen, Barry Reisberg, et al., Arch Neurol, vol. 48, Feb., 1991, pp. 148–154.

Mild Cognitive Impairment in the elderly: Predictors of Dementia, Charles Flicker, Steven H. Ferris, Barry Reisberg, Neurology, vol. 41, No. 7, Jul., 1991.

The Radiologic Prediction of Alzheimer Disease: the Atrophic Hippocampal Formation, M.J. de Leon, J. Golomb, et al., ANJR: 14 Jul./Aug. 1993, pp. 897–906.

FIG. 5

| Measure | Cognitively Normal (GDS 1&2, N = 37) Mean (± SD) | Cognitively Impaired (GDS 3, N = 23) Mean (± SD) | Mild AD (CDS 4, N = 23) Mean (± SD) |
|---|---|---|---|
| Demographic Measures | | | |
| Age | 69.6 (± 8.6) | 73.5 (±8.5) | 71.2 (± 8.4) |
| MMSE | 29.2 (± 1.2) | 27.6 (± 3.1)* | 22.4 (± 4.0)*** |
| Sex (% Male) | 56.8% | 56.5% | 39.1% |
| Noamotor Cognitive Measures | | | |
| Paragraph Recall (Delayed) | 9.9 (± 3.2) | 5.0 (± 3.7)*** | 1.6 (± 2.5)*** |
| Guild Design Recall | 5.9 (± 2.6) | 3.1 (± 2.1)*** | 1.3 (± 1.8)*** |
| Digit Span Forward | 6.5 (± 1.3) | 6.7 (± 1.3) | 6.4 (± 1.2) |
| Digit Span Backwards | 5.3 (± 1.4) | 4.7 (± 1.6) | 3.7 (± 1.2)*** |
| Vocabulary | 68.5 (± 7.9) | 60.0 (± 14.2)* | 47.7 (± 21.4)*** |
| Category Retrieval (Easy) | 19.3 (± 6.3) | 16.0 (± 7.7) | 11.4 (± 4.4)*** |
| Category Retrieval (Hard) | 10.1 (± 3.2) | 8.4 (± 3.7) | 6.2 (± 2.1)*** |
| Motor/Psychomotor Measures | | | |
| Head Tracking (Error Score) (with feedback) | 9.5 (± 6.1) | 13.2 (± 6.5)* | 22.4 (± 13.6)*** |
| Head Tracking (Error Score) (no feedback) | 24.4 (± 8.7) | 37.0 (± 13.4)*** | 45.8 (± 14.4)*** |
| Purdue Pegboard (Assembly) | 28.3 (± 5.7) | 22.5 (± 7.2)** | 15.6 (± 7.8)*** |
| DSST | 55.0 (± 5.8) | 36.5 (± 17.6)*** | 23.5 (± 16.6)*** |
| Head Steadiness (Error Score) | 2.9 (± 2.8) | 3.2 (± 1.4) | 4.0 (± 2.0) |
| Foot Tapping | 51.6 (± 11.7) | 51.1 (± 10.6) | 49.4 (± 13.1) |
| Finger Tapping | 41.4 (± 5.5) | 39.4 (± 6.1) | 35.2 (± 6.1) |

\* $P \leq .05$ (relative to the cognitively normal subjects)
\*\* $P \leq .01$ (relative to the cognitively normal subjects)
\*\*\* $P \leq .001$ (relative to the cognitively normal subjects)

METHOD AND APPARATUS EMPLOYING MOTOR MEASURES FOR EARLY DIAGNOSIS AND STAGING OF DEMENTIA

BACKGROUND OF THE INVENTION

This invention relates to methods for the diagnosis and staging of the severity of dementia using motor and/or psychomotor testing. It employs computerized tests of motor function that are sensitive to very mild levels of non-motor cognitive decline in the elderly.

Dementia is diagnosed and staged by clinical assessment of cognitive and functional capacity. Typical global clinical staging measures are the Global Deterioration Scale (GDS; Reisberg, B., Ferris. S. H., de Leon M. J. and Cook, T., 1982), the Blessed Dementia Scale and Information-Memory-Concentration Test (Blessed, G. Tomlinson B. E., and Roth M., 1968) and the Alzheimer's Disease Assessment Scale (ADAS) (Rosen W., Mohs, R. and Davis, K., 1984). There are also mental status assessments such as the Mini Mental State (Folstein, M. F., Folstein, S. E. and McHugh, P. R., 1975), and various psychological tests such as the Guild Memory Test (Gilbert, J. G. and Levee, R. F., 1971), and the Boston Naming Test (Goodglass, H., Kaplan, E. and Weintraub, S., 1976).

All of these measurements are of limited utility in part because they depend upon the educational attainment and intelligence level of the subject for early diagnosis.

BRIEF DESCRIPTION OF THE PRESENT INVENTION

The present invention enables for the first time, the use of motor/psychomotor test results as early indicators and predictors of dementia and its progress. The invention places minimal demands on cognitive processes related to educational experience, and provides measures more directly related to central nervous system control. Consequently, the current invention can account for "unique variance" either alone or when combined with more traditionally used clinical assessments to identify elderly individuals at risk for future development of dementia.

We have developed methods and apparatus to take advantage of our discovery that certain motor/psychomotor measures differentiate cognitively normal elderly individuals from: (1) non-demented individuals with only mild degrees of cognitive impairment (but who are at heightened risk for the development of dementia in the future and (2) mildly demented patients with Alzheimer's disease (AD), the most frequent cause of dementia in the elderly. Such mild cognitive impairment is discussed in Flicker, Ferris & Reisberg, *Neurology* 41, 1006–009 (1991).

These measures are employed in standard tests of psychomotor function such as the Purdue Pegboard and/or the Digit Symbol Substitution Tests (DSST) of the WAIS-R but more preferably from specialized computer tests of motor function. The Specialized motor tests found most useful in this invention employ computerized tracking paradigms. These tests are more sensitive indices of motor and sensorimotor dysfunction then are the currently employed, traditional clinical neurological measures of psychomotor function. These tests assess the ability to perform: (1) head-tilt tracking maneuvers; (2) balance and weight transfer maneuvers; (3) EMG (Electromyogram) arm-extension tracking maneuvers under isotonic and isometric conditions and (4) wrist joint position matching responses and require the performance of positional maneuvers both in the presence and absence of visual feedback. Objective scores of tracking accuracy are obtained by taking the time integral of error (distance from target over time) and a measure of the variability (lack of steadiness) around the target.

One object of the present invention is to provide a method and apparatus to provide a means of identifying early motor/psychomotor dysfunction in the elderly as a sensitive method for diagnosing and staging mild cognitive decline and mild dementia.

Another object of the present invention is to provide a means for diagnosis of dementia less influenced by education than more traditional assessments of cognitive status.

BRIEF DESCRIPTION OF THE DRAWINGS

FIG. 5 is a table of representative demographic, non-motor cognitive and psychomotor/motor measures of each of three cognitive groups.

DETAILED DESCRIPTION OF A PREFERRED EMBODIMENT

In accord with the present invention, measures were derived from (and norms for detecting cognitive impairment were established relating to) existing tests of motor function (e.g., Purdue Pegboard Test and especially from specialized computerized tests of motor/psychomotor function.

DESCRIPTION OF COMPUTERIZED TESTS OF MOTORIC FUNCTION

Figure 1:
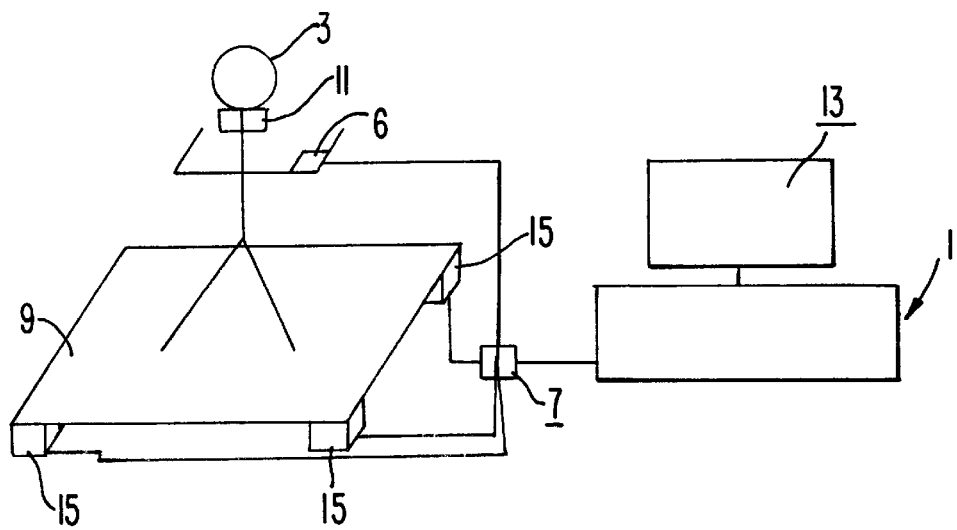
FIG. 1 is a preferred embodiment of the invention.

As shown in FIG. 1, a microprocessor-based system 1 is utilized to interface with monitors collecting information from an individual 3 pertaining to head position, joint position distribution, weight distribution, etc. An electronic goniometer 5 joint position and provides this information to a computer interface 7. The individual stands upon an isometric force platform 9, which is capable of measuring as well as providing feedback to interface 7 and thus to computer 1 concerning such factors as the degree to which weight is symmetrically distributed to the feet, the amount of postural sway present, the smoothness of weight transfer within and between feet. A dual-axis clinometer device 4, is capable of assessment and feedback regarding head position. For each of the devices, the microprocessor-based system 1 monitors and records the accuracy with which a cursor seen on monitor 13 is guided in tracking a target on the monitor. Cursor and target position, as well as tracking error or each trial are recorded and stored in computer 1.

Assessment is conducted over ten trials per task. During assessment, task difficulty is kept constant. The time integral of error is obtained for each trial. This measure represents tracking accuracy and is calculated by integrating cursor/target separation over time. The procedures used to assess body balance weight-shift ability, head position control, EMG-arm extension and joint position are described below.

1. Body Balance Ability

The subject 3 faces a video monitor 13 while standing on a non-movable platform 9 which is mounted on force transducers 15. On the video, positioned at eye level, is display a square-shaped target frame and a square cursor. The subject's task is to move the cursor by performing weight shift maneuvers so that it fits exactly within the target frame. Weight distribution is detected by the force transducers whose output determine the location the location of the cursor on the screen. One task requires that the subject track along the anterior-posterior (A-P) axis. By shifting the center of gravity backwards, the cursor is placed into the target (posteriorly located along the axis).

Ability to track along the lateral and A-P axes concurrently is also tested. The subject stands on the force plate as before. The video screen contains a grid pattern having its origin located at the intersection of the lateral and A-P axes. When weight is uniformly distributed with respect to both the lateral and A-P dimensions, the cursor locates itself at the origin. Any shift in weight distribution displaces the cursor off the origin. The subject must perform weight-shift maneuvers which position the cursor over a stationary target located anywhere on the grid.

2. Head Tracking Ability

For assessment of head control, the subject is seated in front of a video monitor which is positioned at eye level 36 inches away. On the screen 13 a square cursor is displayed, located at the intersection of the lateral and A-P axes, and a square-shaped target frame, located in the upper right quadrant. The cursor moves in response to head tilt monitored by dual axis clinometer transducer 11. It is displaced upward when the head tilts forward, downward when it tilts backward, and laterally left or right according to the orientation of the head. Tracking along the lateral and A-P axes concurrently is required. With the head in the upright position with respect to both the lateral and A-P dimensions the cursor locates itself at the origin. Any shift in head position displaces the cursor off the origin. The subject must perform head-tilt maneuvers which position the cursor over the stationary target. During each trial the coordinate values corresponding to position of the cursor and target are monitored and stored on a recording medium such as a floppy disk.

3. Head Steadiness

Using the same procedures and equipment that are employed in the head tracking paradigm, the subject is required to maintain the position of the square cursor inside the square-shaped target frame by holding its head as steady as possible. This task does not require the more complex head-tracking movements needed in the previously described example.

4. EMG-Arm Extension Tracking

The procedure employed assesses the ability to control arm extension (EMG output of triceps muscle) while inhibiting contracting the flexor muscles of the arm (EMG output of biceps muscle). The task is run under four conditions: (1) isometric extension with on-line visual feedback; (2) isometric extension without feedback; (3) isotonic extension with on-line visual feedback; and (4) isotonic extension without feedback. All trials are followed by delayed knowledge of results. The task requires the subject to extend the dominant arm which causes a boxed-shape cursor on a computer monitor to move vertically upward toward a stationary target box. The subject must try to superimpose the cursor over the target as quickly and accurately as possible. The score is the time integral of error over each of the ten 9-second trials per condition.

5. Joint Position Matching

Information concerning muscle length and its rate of change can be interfered with through the application of vibration sufficient to produce high-frequency muscle spindle discharge. Afferent information from primary muscle spindle endings contributes to determining terminal joint position. Hence, a constant error in desired limb position results when vibration is applied to an antagonist acting on a joint during movement.

Figure 2:
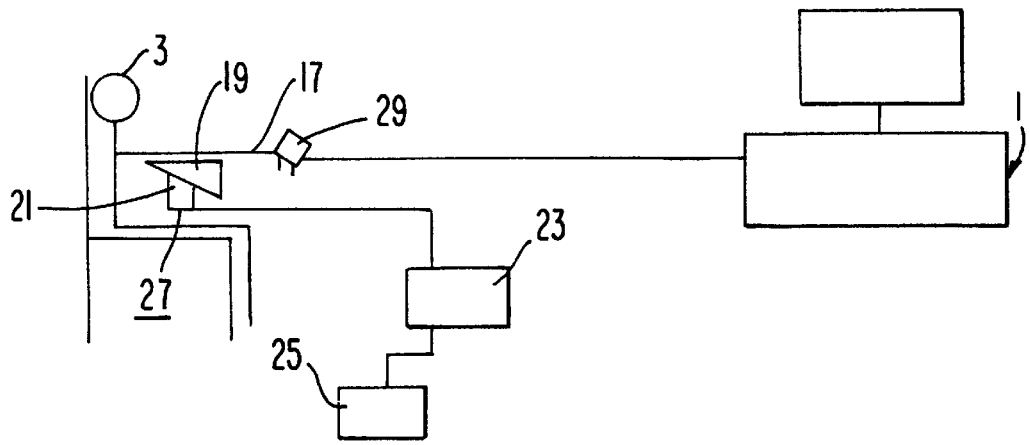
FIG. 2 is a second preferred embodiment of the invention.
Figure 3:
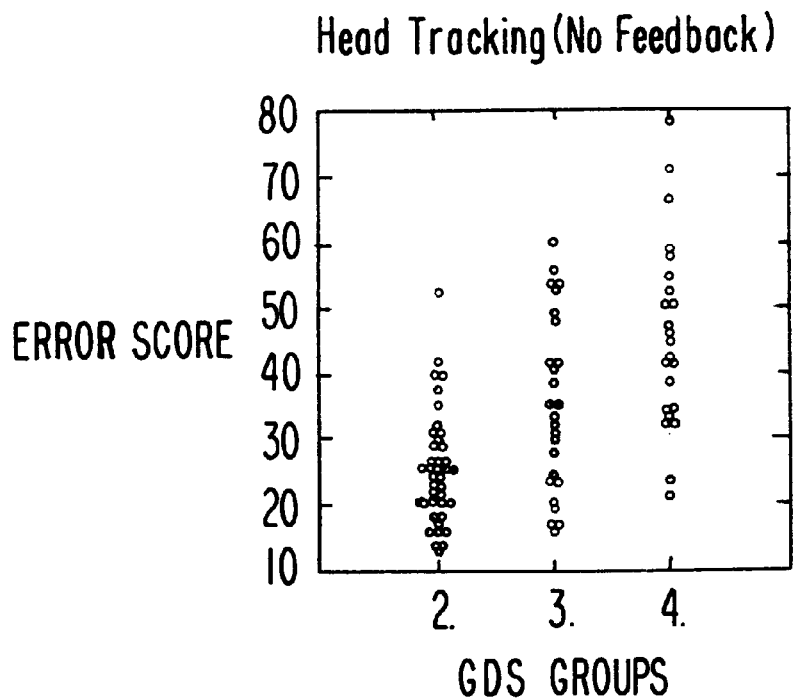
FIG. 3 is a graph of head tracking data.
Figure 4:
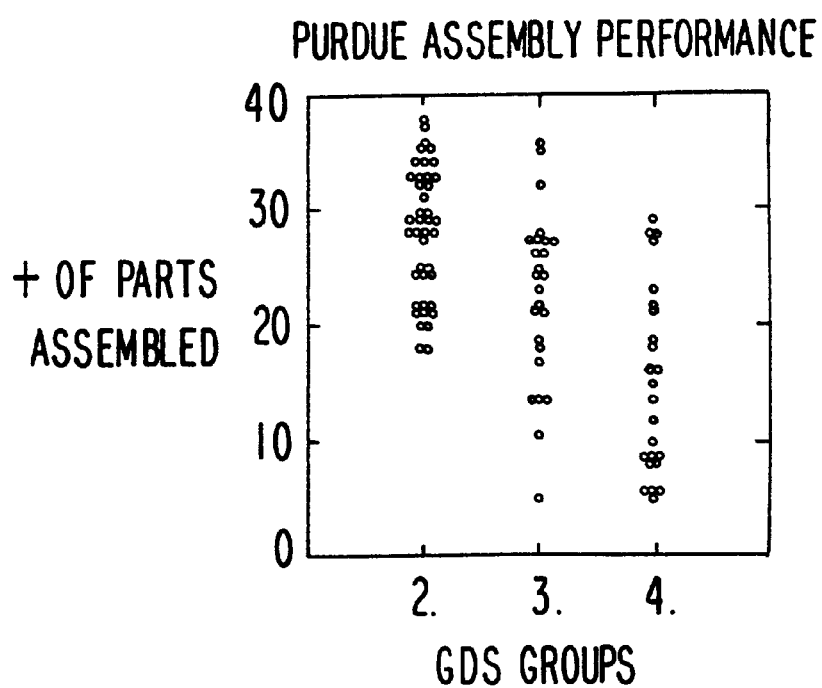
FIG. 4 is a graph of Purdue Assembly Performance.

Subjects respond with the preferred arm and are not given feedback concerning reproduction accuracy during the session. Nor are they permitted to view their wrist while responding. As shown in FIG. 2, they are tested while seated with the arm in the forward position and the forearm 17 pronated. A wedge-shaped foam pad 19 (rising from the elbow at a 30 degree incline and attached to a table of adjustable height) supports the arm. A mechanical vibrator 21 (Bruel & Kjaer Type 4810), its actuator providing distal support, forms a continuous bridge with the foam wedge. So positioned, the actuator maintains constant contact with the flexor tendons of the wrist. Vibration is delivered perpendicularly to the skin at a point two inches from the distal wrist crease. The vibrator is sine-wave driven at 100 Hz by a low frequency oscillator 23 (Hewlett Packard Type 202C) via a power amplifier 25 (McIntosh Type MC75). Vibration frequency is confirmed by means of an electronic counter 27 (Hewlett Packard Type 5221A). The stimulus variables (i.e., frequency, intensity, extent) are selected in order to produce high-frequency muscle spindle discharge sufficient to interfere with information conveyed by spindle afferents to the central nervous system.

The initial starting position, reference response and matching response are monitored by an electrogoniometer 29 spanning the carpophalangeal joint. This parallelogram-type device interfaces with a microcomputer 1 (Southwest Technical System 6809) with which the data are collected and analyzed. Prior to each response, the subject is seated with the hand hanging relaxed in palmar flexion in the starting position. When the computer program confirms that the subject's wrist is properly located at the starting position, it commences a three-second countdown followed by a 100 ms tone which signals the subject to respond. Each response, whether reference or matching, must be completed within a second, whereupon another tone will sound.

During establishment of the reference response for each trial, subjects are required to extend the wrist within a specified 20-degree band, ranging from 10 to 30 degrees. Any response within this range is established as the reference response for that trial. If the computer program confirms that the response falls within the required band, the subject is immediately instructed to return the wrist to the starting position and, at the sound of the tone, to try to exactly replicate the just performed response. If the reference response falls outside the required band, then the subject will be informed that it is too large or too small, and the attempt repeated.

Reproductive accuracy of joint position is determined by the constant error (CE). The magnitude and sign of the constant error (the average extent to which the reference response is either undershot or overshot) are calculated by subtracting the value of each trial's reference response from its corresponding matching response.

EXAMPLES

We have discovered an association between motor change and very mild cognitive dysfunction. FIG. 5 shows representative demographic, non-motor cognitive and psychomotor/motor measures of each of the three cognitive groups. These groups do not differ in age, sex distribution or presence of white matter lesions. Of special interest is the contrast between the controls and the mildly cognitively impaired group. It is important to note that the mildly impaired (GDS=3) subjects manifest a very mild degree of cognitive dysfunction, as is illustrated by a mean Mini Mental State Exam (MMSE) score of 27.6. Many of our motor measures such as head tracking (especially when performed without feedback and potentially relying to some degree on motor memory), Purdue Peg Board performance (especially the Assembly subtest which requires coordinated flexible fine motor responses), Digit Symbol Substitution Test (DSST) performance and other measures requiring higher order motor functioning, appear to differentiate the controls from the mildly impaired. In fact, employing small combinations of two or three of these motor/psychomotor measures identified in a stepwise multiple regression predicting cognitive group membership (i.e., GDS 1&2 vs. GDS=3), produces multiple r values greater than 0.6 ($p<0.001$). These values are higher than correlations between the MMSE and cognitive group membership and are very close to the correlations between our non-motor cognitive measures of memory and language and group membership. Furthermore, some of the motor measures add significantly to the multiple correlations obtained by non-motor cognitive measures alone. These observations indicate that motor/psychomotor change is as much a part of early cognitive decline as are changes in memory and language function, provided that sensitive tests of motor function are employed. (Note that measures of gross motor speed, steadiness and body strength do not differentiate the controls from the mildly impaired cases.) This invention may help in the early detection of significant cognitive decline in the elderly, especially when combined with other predictors. The identification of mild cognitive impairment is especially important in light of recent reports that more than half of these cases will develop dementia over the follow-up interval of several years. Motor data show that there is a fairly wide variability in some of our sensitive motor tests, with some of the mildly impaired scoring more like the average control subjects and others more similar to patients with mild AD.

While there have been shown and described and pointed out the fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A method for differentiating cognitively normal elderly individuals from mildly demented patients with Alzheimer's disease comprising placing head tilt monitoring means on the individual and facing the individual towards a video monitor;

positioning on said video monitor a target frame and cursor, said cursor position controlled by the head tilt of the individual;

monitoring head tilt by the individual by detecting signals from said head tilt monitoring means said signals being indicative of said cursor position;

converting signals obtained during said monitoring step into measures of ability to maintain said cursor within said target frame.

2. The method for differentiating cognitively normal elderly individuals from mildly demented patients with Alzheimer's disease of claim 1, wherein said individual attempts to hold its head steady.

3. A method for creating measures of motor/psych-motor performance comprising placing head tilt monitoring means on the individual and facing the individual towards a video monitor;

positioning on said video monitor a target frame and cursor, said cursor position controlled by the head tilt of the individual;

monitoring head tilt by the individual by detecting signals from said head tilt monitoring means, said signals being indicative of said cursor position;

converting signals obtained during said monitoring step into measures of ability to maintain said cursor within said target frame.

4. A method for creating measures of motor/psych-motor performance of claim 3, wherein said individual attempts to hold its head steady.

* * * * *